(12) United States Patent
Goh et al.

(10) Patent No.: US 6,737,053 B1
(45) Date of Patent: May 18, 2004

(54) TISSUE-ENGINEERED LIGAMENT

(75) Inventors: James Cho Hong Goh, Singapore (SG); Kwan-Ho Chan, Lubbock, TX (US)

(73) Assignee: National University of Singapore (SG)

( * ) Notice: Subject to any disclaimer, the term of this patent is extended or adjusted under 35 U.S.C. 154(b) by 0 days.

(21) Appl. No.: 09/710,435

(22) Filed: Nov. 10, 2000

Related U.S. Application Data

(60) Provisional application No. 60/165,331, filed on Nov. 12, 1999.

(51) Int. Cl.⁷ .................................................. C12N 5/00
(52) U.S. Cl. ........................ 424/93.7; 623/11; 623/11.1; 623/13
(58) Field of Search ............................ 424/93.7; 623/11, 623/13, 11.1

(56) References Cited

U.S. PATENT DOCUMENTS

| | | | | |
|---|---|---|---|---|
| 4,411,027 A | * | 10/1983 | Alexander et al. | 3/1 |
| 4,759,765 A | * | 7/1988 | Van Kampen | 623/13 |
| 5,078,744 A | | 1/1992 | Chvapil | |
| 5,376,118 A | * | 12/1994 | Kaplan et al. | 623/11 |
| 5,425,766 A | * | 6/1995 | Bowald | 623/13 |
| 5,855,619 A | * | 1/1999 | Caplan et al. | 623/11 |
| 6,077,989 A | | 6/2000 | Kandel et al. | |
| 6,106,556 A | | 8/2000 | Demopulos et al. | |
| 6,123,727 A | * | 9/2000 | Vacanti et al. | 623/13 |
| 6,174,333 B1 | * | 1/2001 | Kadiyala et al. | 623/11.11 |
| 6,482,231 B1 | * | 11/2002 | Abatangelo et al. | 623/11.11 |

* cited by examiner

*Primary Examiner*—Jean C. Witz
(74) *Attorney, Agent, or Firm*—Pandiscio & Pandiscio

(57) ABSTRACT

An apparatus and method for the reconstruction of a previously torn ligament using a tissue-engineered ligament. The tissue-engineered ligament includes a scaffold of biocompatible material having at least one layer and forming a sheet. The scaffold is placed in a cultured medium for seeding with fibrocyte forming cells. The seeded scaffold is then placed in an incubator to increase the number of cells. The seeded scaffold is then formed into a slender structure suitable for implantation. The method of making a tissue-engineered ligament includes forming a scaffold of biocompatible material having at least one layer forming a sheet. Next, the scaffold sheet is seeded with fibrocyte forming cells. The method further includes increasing the number of cells on the seeded scaffold and forming a slender structure suitable for implantation from the scaffold.

53 Claims, 8 Drawing Sheets

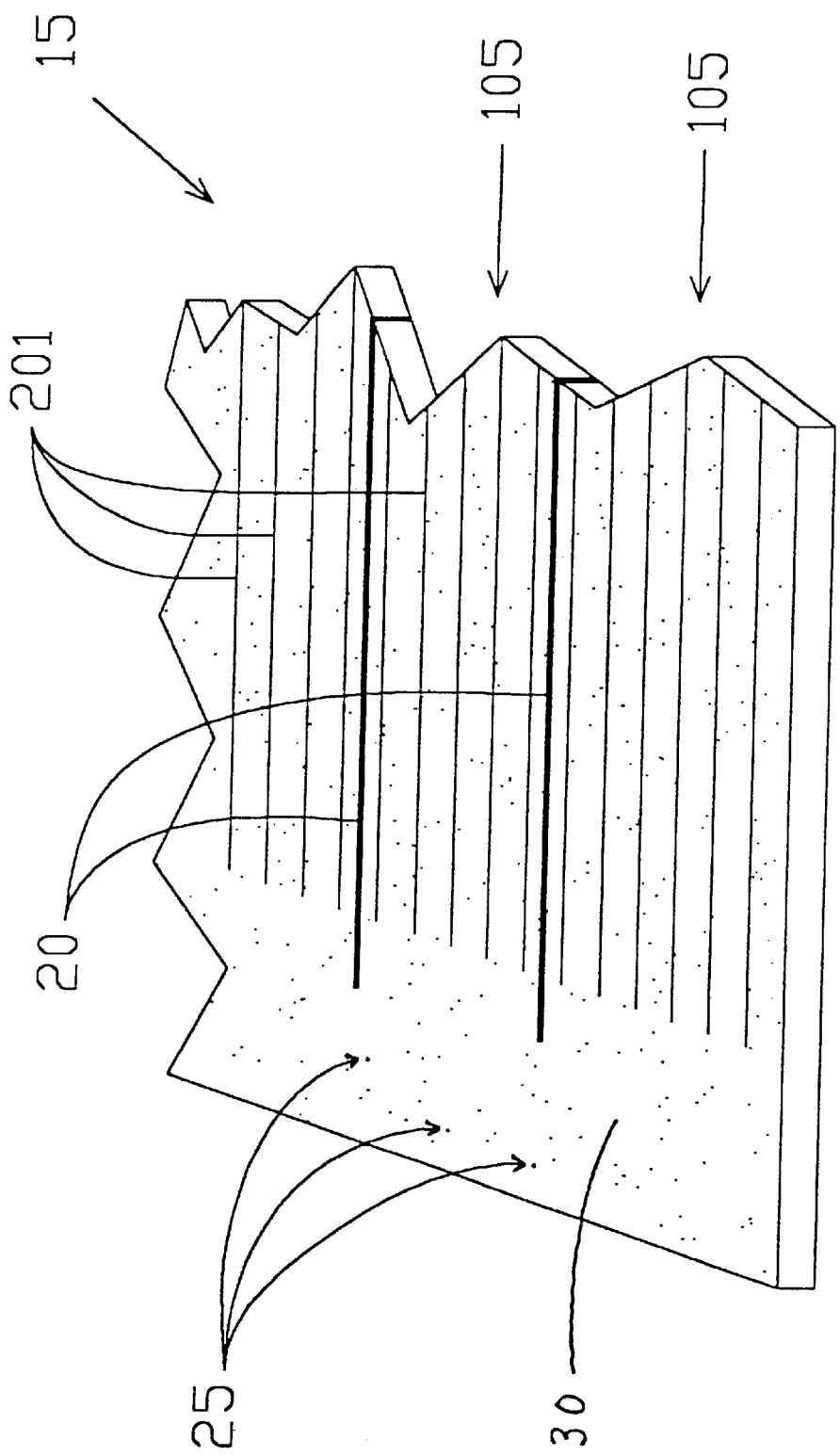

Section A-A

TISSUE-ENGINEERED LIGAMENT

REFERENCE TO EARLIER APPLICATION

This application claims the benefit of U.S. Provisional Patent Application Serial No. 60/165,331, filed Nov. 12, 1999 by James Cho Hong Goh and Kwan-Ho Chan. The aforementioned document is hereby incorporated herein by reference.

FIELD OF THE INVENTION

This invention generally relates to apparatus and methods for the manufacture of replacement tissue using tissue engineering methods. More particularly, this invention relates to apparatus and methods for the manufacture of tissue-engineered ligaments suitable for the treatment of ligament deficiencies in patients.

BACKGROUND OF THE INVENTION

Men and women who are athletically active experience the majority of ligament tears, particularly tearing of the anterior cruciate ligament of the knee. The anterior cruciate ligament is commonly torn by forces applied to the knee during twisting, cutting, deceleration or tackling. A torn anterior cruciate ligament will generally not heal. An anterior cruciate deficient knee is often unstable during pivoting activity. Repeated instability episodes of the knee may lead to further damage of the articular surface and cause tearing in the menisci. It is therefore desirable to stabilize the knee by reconstructing a torn anterior cruciate ligament. Attempts in the past to directly repair the torn anterior cruciate ligaments have been relatively ineffective. Prosthetic ligament replacements made of carbon fibers and Gore-Tex materials do not last a long period of time. Repeated loading of a prosthetic ligament in a young active patient leads to failure of the ligament. The release of debris from a failed ligament results in chronic inflammation of the joint, and osteolysis of bone, in and around the area of ligament attachments.

The current standard practice is to reconstruct a torn anterior cruciate ligament by substituting the torn ligament with a patient's own tissue. The middle third of the patellar tendon or the hamstring tendons are commonly used as substitution ligaments. Alternatively, the allograft patellar tendon, hamstring tendon or Achilles tendon from a donor can be used for reconstructing the ligament. However, donor materials are associated with a risk of infectious disease transmission such as AIDS. Using a patient's own tissue is also associated with morbidity at the donor site. For example, stress fracture of the patellar, quadriceps muscle weakness and a long rehabilitation period may result from the use of a patient's own tissue. Furthermore, harvesting and preparation of autogeneous tissue prolongs surgery time.

Previous attempts to use an artificial stent to replace a damaged anterior cruciate ligament have not been successful. One such example is the LAD Prosthetic Ligament, which was used as a scaffold for tissue ingrowth. The LAD Prosthetic Ligament is not bioabsorbable. Therefore, whatever initial fibrous tissue that forms on the LAD Prosthetic Ligament is not subject to accommodating increasing loads and there is no stimulus for the fibrous tissue to proliferate to support increasing loads. Furthermore, the LAD Prosthetic Ligament is not an optimal structure for tissue ingrowth.

Recent progress in tissue engineering has made it possible to harvest cells from a patient's own body or a donor. The harvested cells are then grown into the desired tissues on three-dimensional scaffolds, or hydrogel carriers, made of biodegradable polymers. These tissues include, but are not limited to, heart muscles, fat, cartilage, and skin. The tissue grown outside of the body, together with the scaffold containing the tissue, is then transplanted into the patient to correct an existing defect. After transplantation, the cells may further replicate, reorganize and mature, depending on the environment of the host bed into which the cells were transplanted.

Two good sources of cells that are suitable for tissue engineering are embryonic stem cells and mesenchymal stem cells. These stem cells, when exposed to particular bioactive factors, also known as growth factors, can be directed to differentiate into different types of cell lines in a predictable way. For example, mesenchymal stem cells can be directed to differentiate into different types of tissue such as, but not limited to, skin, tendon, ligament and bone under suitable conditions. These conditions include exposing cells to certain growth factors. It is known that mesenchymal cells are directed to differentiate into fibroblast when exposed to interleukin. Furthermore, fibroblast is only able to differentiate into fibrocytes that are the mature cells of ligament tissue.

Mesenchymal cells are present in very small numbers in bone marrow, periosteum, skin and muscle. A small piece of the tissue containing a small number of mesenchymal cells is preferably harvested from the patient's own body. For example, a piece of periosteal tissue harvested from the patient or donor is morsellised into small pieces. Using tissue culture, techniques well known to those skilled in the art, the mesenchymal cells are isolated and the number of cells expanded. The mesenchymal cells are then seeded onto scaffolds. These scaffolds are preferably made of biodegradable materials to make the desired tissues.

There are two major challenges in growing tissue-engineered ligaments outside the body. First, most cells cultured in vitro tend to grow in a monolayer. Even if it is possible to culture tissue to a few millimeters thick, deeper layers of the cells may not have sufficient supplies of nutrients. Secondly, it is difficult to adequately and uniformly seed the scaffold with cells to initiate cell expansion.

It is, therefore, an object of the present invention to provide tissue-engineered ligaments for reconstruction of previously torn ligaments.

It is another object of the present invention to provide tissue-engineered ligaments to reduce the time it takes to complete the surgery and to eliminate donor site morbidity in the patient.

It is still another object of the present invention to provide tissue-engineered ligaments grown from a small amount of tissue obtained from the patient.

It is another object of the present invention to provide a scaffold for uniform and adequate seeding of cells to initiate cell expansion for making tissue-engineered ligaments.

It is also another object of the present invention to provide a scaffold for a tissue-engineered ligament with adequate channels for nutrients to reach the cells.

It is also another object of the present invention to provide a method to enhance the growth and alignment of the fibrocytes and the extra cellular matrix during incubation of the tissue-engineered ligament.

Another object of the present invention is to provide tissue-engineered ligaments that will permanently anchor to a patient's bone.

Yet another object of the present invention is to provide tissue-engineered ligaments that will mature and resist physiological load across the joint.

Still another object of the present invention is to provide a method of making tissue-engineered ligaments.

SUMMARY OF THE INVENTION

The present invention comprises an apparatus and method for the reconstruction of a previously torn ligament using a tissue-engineered ligament. The tissue-engineered ligament includes a scaffold of biocompatible material having at least one layer and forming a sheet. The scaffold is placed in a cultured medium for seeding with fibrocyte forming cells. The seeded scaffold is then placed in an incubator to increase the number of cells. The seeded scaffold is then formed into a slender structure suitable for implantation. The method of making a tissue-engineered ligament includes forming a scaffold of biocompatible material having at least one layer forming a sheet. Next, the scaffold sheet is seeded with fibrocyte forming cells. The method further includes increasing the number of cells on the seeded scaffold and forming a slender structure suitable for implantation from the scaffold.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 2A is a schematic diagram illustrating longitudinal microchannels contained in a ligament scaffold as shown in FIGS. 1–4;

DETAILED DESCRIPTION OF THE PREFERRED EMBODIMENTS

Figure 1:
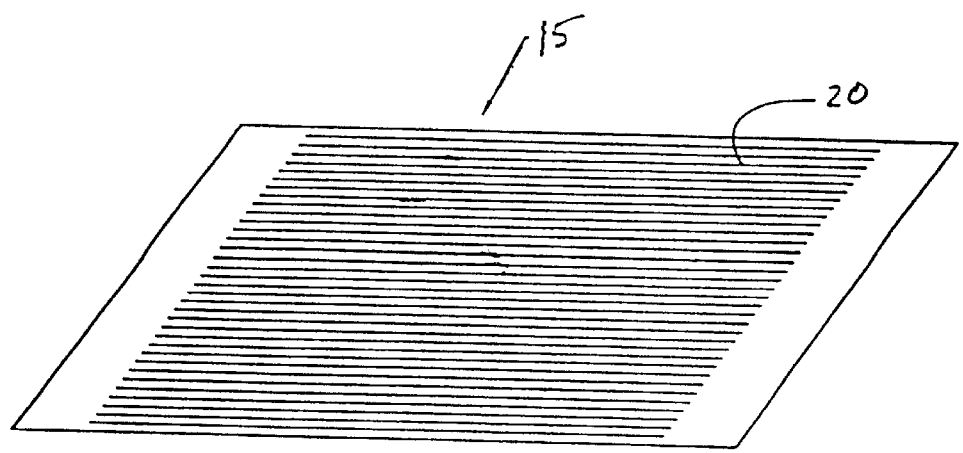
FIGS. 1–4 are schematic diagrams of a preferred embodiment of the present invention illustrating a construction of a ligament scaffold.
Figure 2:
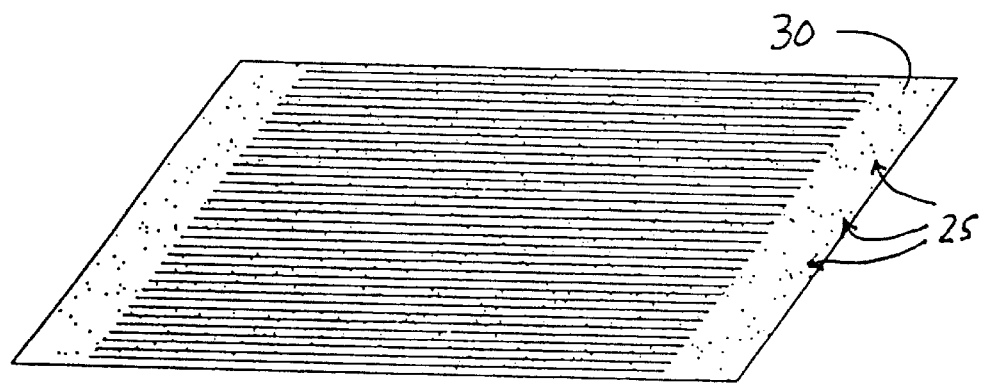
Figure 3:
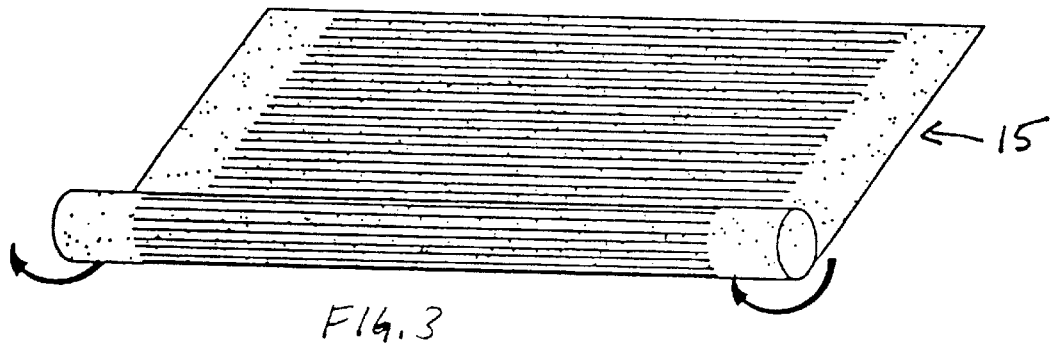
Figure 4:
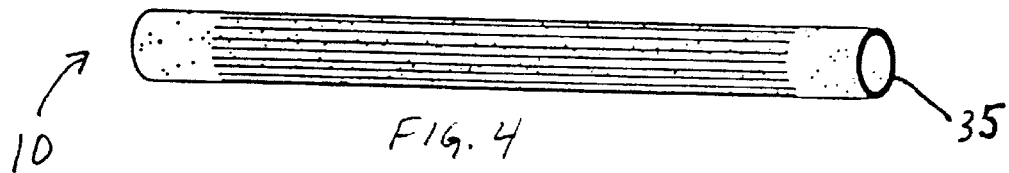
Figure 5:
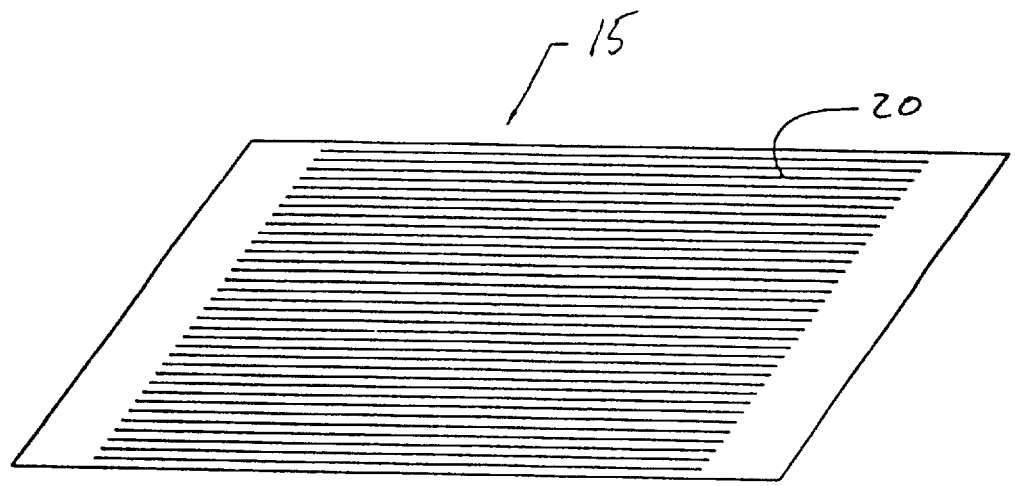
FIGS. 5–8 are schematic diagrams of another preferred embodiment of the present invention illustrating a construction of a ligament scaffold.
Figure 6:
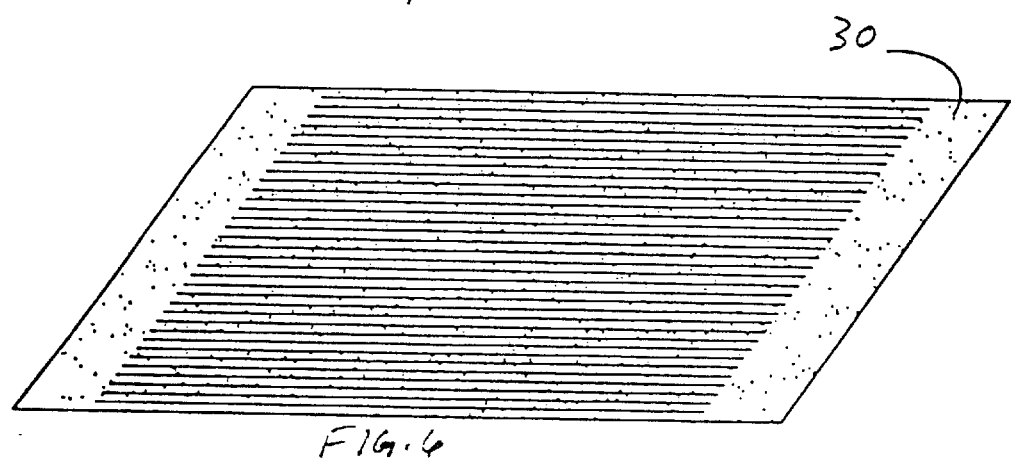
Figure 7:
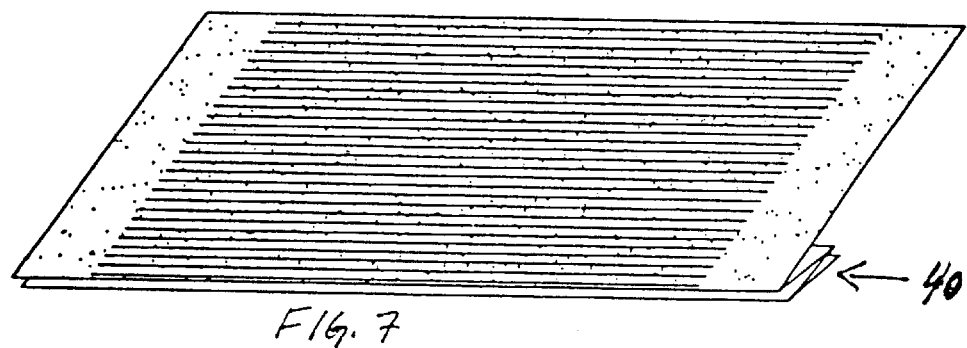
Figure 8:
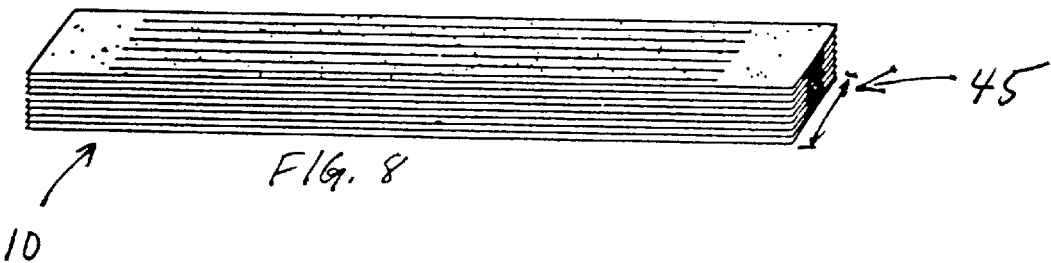
Figure 9:
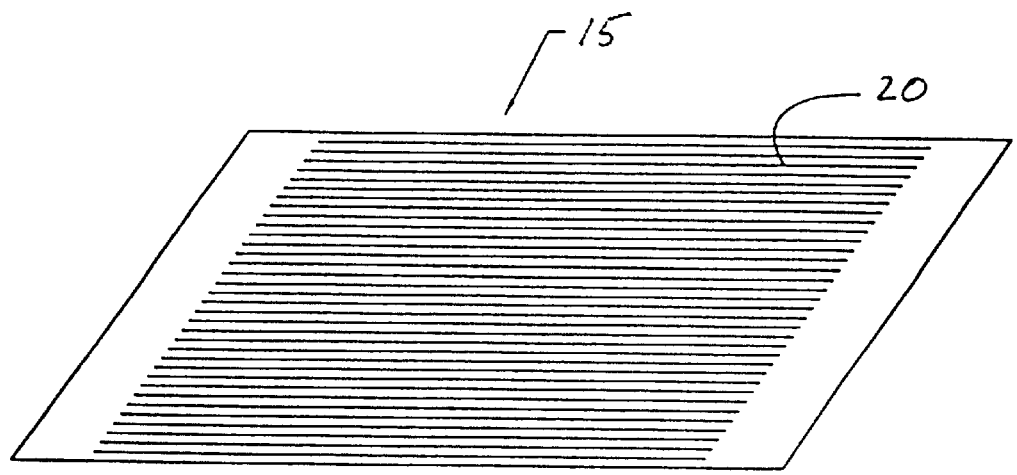
FIGS. 9–12 are schematic diagrams of another preferred embodiment of the present invention illustrating a construction of a ligament scaffold.
Figure 10:
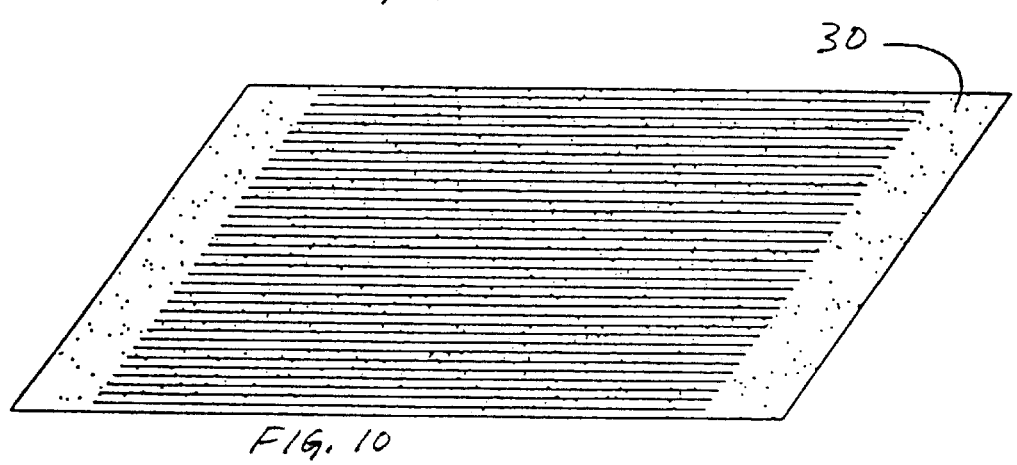
Figure 11:
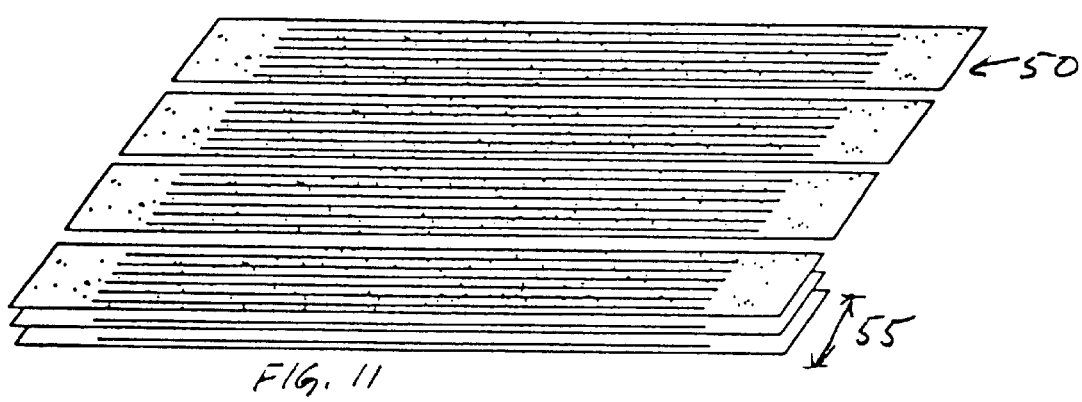
Figure 12:
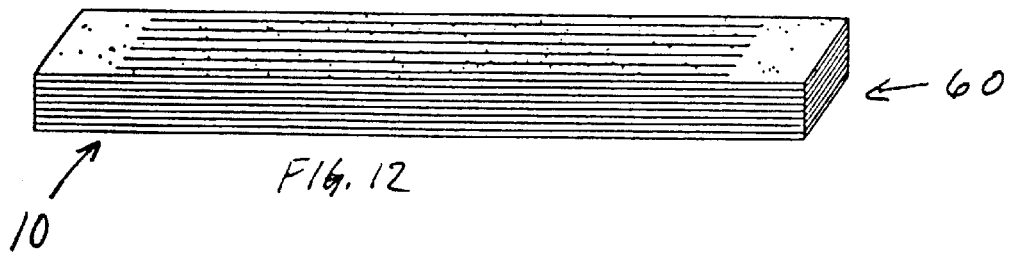

Referring first to FIGS. 1–12, the starting material for a tissue-engineered ligament 10 is a sheet 15 of biocompatible material which is preferably bioabsorbable. The sheet 15 may also be a porous structure. The pores of the porous structure may be partially or fully interconnected across the thickness of the sheet. The pore structure essentially forms perforations when fully and directly interconnected across the thickness of the sheet. A sheet of woven fabric made of a biocompatible and preferably biodegradable material is an example of such a construct. Additionally, the sheet may contain slits 20 which extend completely through sheet 15. A method of forming a tissue-engineered ligament includes placing the biocompatible sheet 15 in a cultured medium and seeding the sheet with fibrocyte forming cells 25 (FIG. 2). Next, the seeded sheet is incubated to increase the number of fibrocyte forming cells. After a sufficient cell increase, sheet 15 is reformed into a slender structure 35, such as a tissue-engineered ligament suitable for implantation into a patient. In this respect it should be appreciated that the presence of slits 20 in sheet 15 permit nutrients and the like to pass readily into the interior of slender structure 35. In addition, slits 20 permit cells 25 to grow through sheet 15. Furthermore, the presence of slits 20 provides greater flexibility to slender structure 35, whereby it may function more like a natural ligament. If there is sufficient porosity in biocompatible sheet 15, additional perforations or slits may not be necessary for diffusion of nutrients to cells 25 when sheet 15 is formed into slender structure 35.

The first embodiment of the invention shown in FIGS. 1–4 provides rectangular sheet 15 of biocompatible material with multiple longitudinal slits 20 precut into the material. Slits 20 start and end at a prescribed distance from the edge of rectangular sheet 15, thereby leaving uncut margins 30 connecting the adjacent strips as shown in FIG. 2. The whole construct is immersed in culture medium solution (not shown) and then seeded with fibrocyte forming cells such as mesenchymal stem cells or fibroblast cells. When a sufficient quantity of fibrous tissue has formed, sheet 15 is rolled into a slender structure 35, preferably with the strips oriented longitudinally and the uncut edges 30 forming the ends of the slender structure. Slender structure 35 is then implanted into a patient to reconstruct a missing ligament. Slender structure 35 may be further incubated prior to implantation to allow for further growth of fibrous tissue. Alternatively, slender structure 35 can be implanted in a penultimate location in a patient's body such as the peritoneal cavity, muscle bed or any other soft tissue bed. This implantation allows further growth of fibrous tissue prior to implantation in a functional location, such as the knee joint for reconstruction of the anterior cruciate ligament.

Other methods of forming slender structure 35 from sheet 15 are also possible. Examples include, but are not limited to, folding sheet 15 back and forth in an accordion style fold 40 with a width 45 corresponding to the desired width of tissue-engineered ligament 10 as shown in FIGS. 5–8, or cutting sheet 15 into strips 50 corresponding to a desired width 55 of tissue-engineered ligament 10 and stacking one strip 50 on top of another, thereby forming stack 60 as shown in FIGS. 9–12.

The fibrocyte forming cells can be harvested from a human donor. Preferably, fibrocyte forming cells are harvested from the patient's own body. Fibrocyte forming cells, which include mesenchymal stem cells or fibroblast cells, can be derived from a number of sources such as skin, bone marrow and periosteum.

The biocompatible material of sheet 15, which is preferably also a bioabsorbable material, can be, but is not limited to, one or more of the following: polyglycolic acid, polylactic acid, a mixture of PGA/PLA, chitin and collagen. This material may also be porous. Sheet 15 may comprise a uniform structure, a woven structure, a composite structure (e.g., a sheet with incorporated filaments, including aligned filaments such as for reinforcement), etc. Flat sheets 15 of autograft or allograft tissue may also be used. One example is fascia lata. The fascia lata tissue can be preprocessed to reduce reaction. Several methods, including freeze-drying, exist for preprocessing fascia lata.

The biocompatible material of sheet 15 may also be coated with collagen and other factors to promote adhesion of the fibrocyte forming cells 25. The expansion of the number of cells can be promoted by the addition of growth factors to the biocompatible material of sheet 15 or the culture medium.

To induce mesenchymal cells to differentiate into fibroblast, fibroblast growth factors such as interleukin may be added to the biocompatible material or the culture medium.

The strength of the cultured fibrous tissue is made stronger by orientating the growth of the fibrocytes and deposition of the collagen fibers in the longitudinal direction of the slender structure. The fibrocytes are induced to orientate longitudinally by incorporating longitudinal microchannels 201 (FIG. 2A), with a width and depth of the order 1 to 200 microns, on the surface of the biocompatible material of sheet 15. The longitudinal microchannels 201 encourage the fibrocytes to cluster along the microchannels and, additionally, urges the fibrocyte cells to orient themselves parallel to the axis of the microchannels. The application of cyclic loading to the biocompatible materials during incubation further enhances orientation of the cells and collagen fibers. Cyclic loading can also increase the growth of the fibrous tissue. The cyclic loading can be applied to the biocompatible material in the rolled or unrolled configuration. It is to be noted that when the slender structure is loaded in longitudinal tension, the strips 105 will be taut and fluid will be forced out through the perforations or slits. When the tension is released or lessened, the slender structure tends to assume a slightly larger diameter, thus permitting fluid to flow into the slender structure through the slits or perforations. Such cyclic loading will create an environment of circulating fluid providing fresh nutrient fluid to the cells within the slender structure. Additionally, the cells suspended in the fluid for seeding are carried by the circulating fluid into the interior of the slender structure 35 thereby increasing the chance of cells attaching in the interior of the slender structure 35.

In an alternative embodiment of this invention (not shown), fibrocyte forming cells 25 on the biocompatible material of sheet 15 are cultured and, when a sufficient expansion of cells 25 is achieved, slits 20 are then made in the sheets as described above. Some of cells 25 will be damaged during the creation of slits 20. This damage is compensated for by the more efficient cell expansion on an uninterrupted (i.e., slit-less) flat surface during the incubation period.

In order to increase the rate at which the number of cells 25 increase, the mesenchymal stem cells or fibroblast can be genetically altered to increase local production of desired growth factors. This can be done by viral transfection or by incorporating plasmid genes into the matrix of the biocompatible material.

Figure 13:
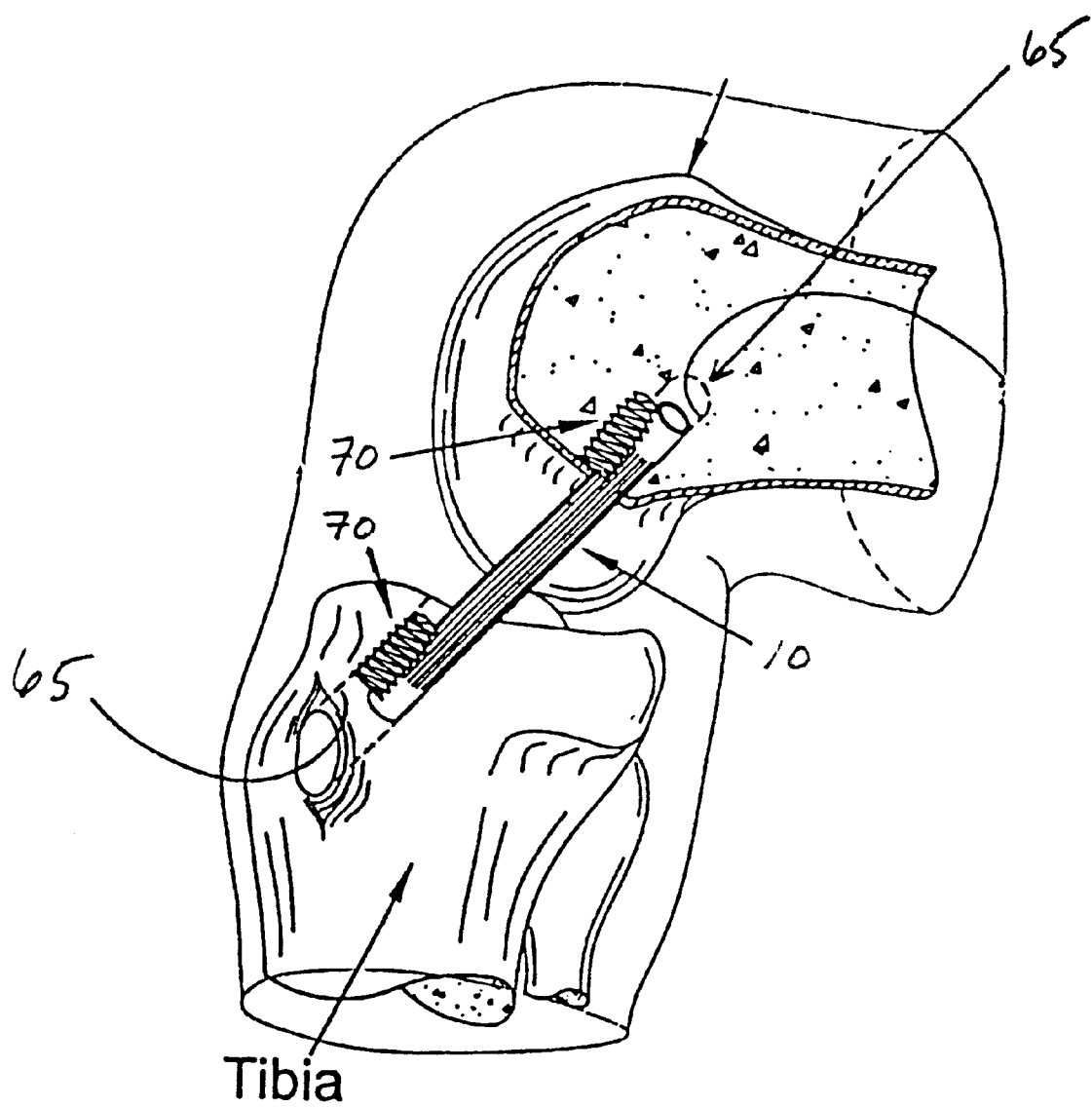
FIG. 13 is a schematic diagram of a preferred embodiment of the present invention illustrating a fixation of a tissue-engineered ligament with interference screws.

Now looking at FIG. 13, the ligament 10 is ready for transplantation into a patient after incubating cells 25 attached to scaffold sheet 15. Incubation usually occurs for a period of time ranging from one to twelve weeks to allow substantial growth and expansion of cells 25. In general, as shown in FIG. 13, two bone tunnels 65 are prepared during surgery on opposite sides of the joint using techniques well known in the art. The ligament 10 is then fixed in the bone tunnels 65 with an interference screw 70 at both ends. This is similar to the fixation of hamstring ligaments with an interference screw in standard arthroscopic anterior cruciate reconstruction. Alternatively, if desired, other surgical techniques well known in the art may be used to secure the tissue-engineered ligament 10 within the knee joint. Without harvesting autologous tissue, such as the patellar tendon or hamstring tendons, the complexity and time required for completing this surgery is greatly reduced. Also any morbidity associated with the harvesting of autologous tendon is eliminated.

After successful implantation of tissue-engineered ligament 10, further growth of the fibroblast and fibrocytes will further anchor ligament 10 in the bone tunnels 65 by tissue ingrowth. Also repeated cyclic loading will encourage hypertrophy of tissue-engineering ligament 10. With time, the scaffold sheet 15 will be gradually absorbed and the entire load across the joint will eventually be carried by tissue-engineered ligament 10. Ligament 10 is a live tissue and will eventually mature into a more stable structure capable of resisting normal transient increases in physiologic load.

Figure 14:
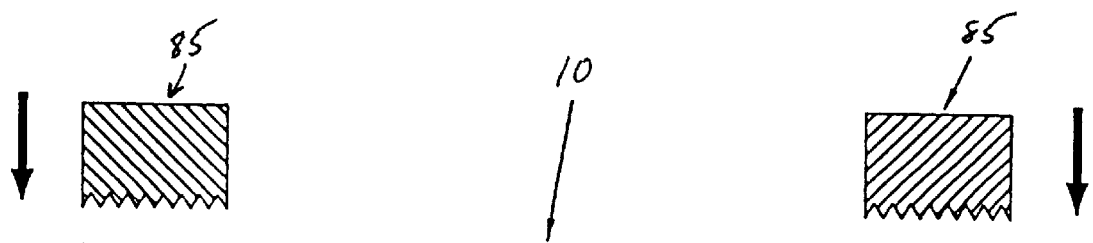
FIGS. 14–16 are schematic diagrams of a preferred embodiment of the present invention illustrating molding of threads into both ends of a tissue-engineered ligament.
Figure 15:
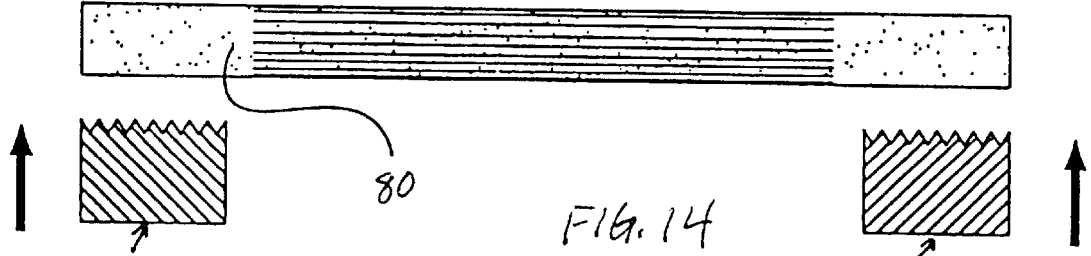
Figure 16:
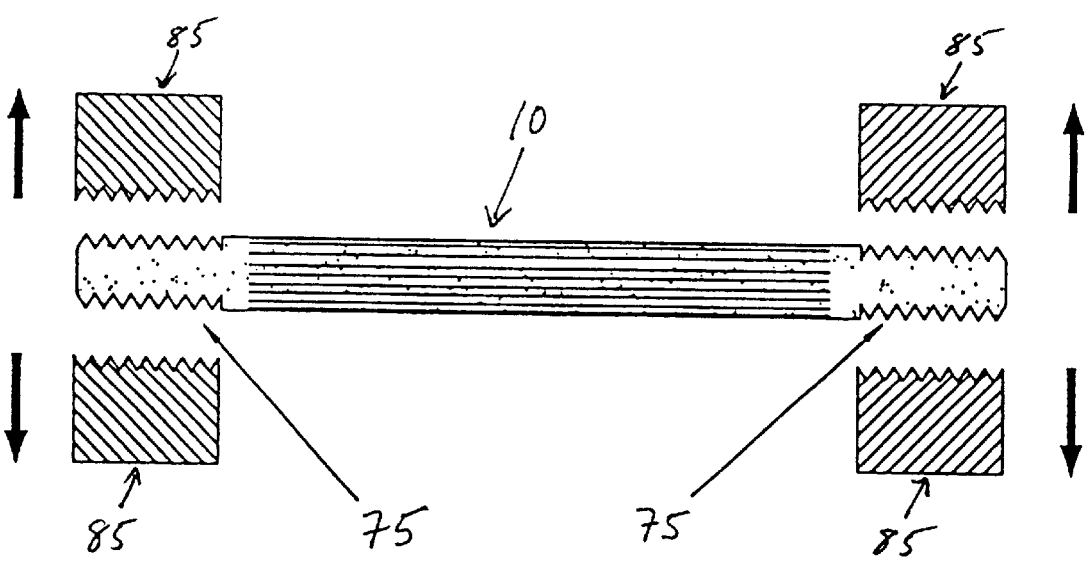
Figure 17:
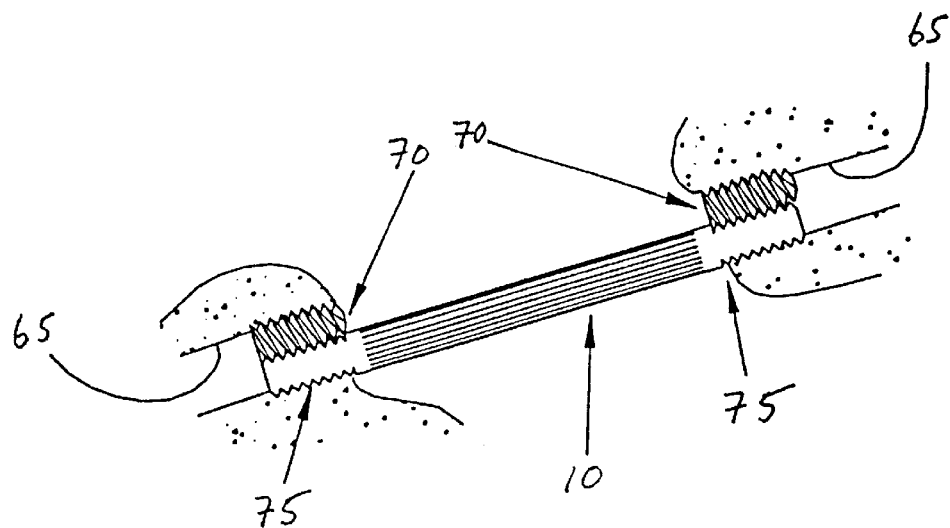
FIG. 17 is a schematic diagram of a preferred embodiment of the present invention illustrating threaded ends of a tissue-engineered ligament engaging interference screws and the wall of a bone tunnel.

Now looking at FIGS. 14–16, fixation can be enhanced by molding threads 75 into the ends 80 of slender structure 35 using a molding device 85 before implantation. Threaded ends 75 of tissue-engineered ligament 10 engage the thread of interference screw 70, as seen in FIG. 17. Advancement of interference screw 70 urges threaded end 75 of tissue-engineered ligament 10 against the wall of bone tunnel 65 and causes threads 75 of end 80 of tissue-engineered ligament 10 to embed into bone tunnel 65. This action further enhances fixation. Alternatively, a rigid body (not shown) secured to the end of the tissue-engineered ligament may be provided for an interference screw to press against to provide fixation. The rigid body may contain threads corresponding to the screw. Alternatively, the rigid body may not have any threads.

In a preferred embodiment, the starting material is a thin rectangular sheet 15 of a biocompatible material including a biodegradable polymeric material, a natural material, and/or an allograft or autograft fascia lata material. Examples of biodegradable polymeric materials include, but are not limited to, PGA, PLA, or mixture of PLA/PGA, etc. Examples of natural materials include, but are not limited to chitin, chitosan, etc.

Figure 18:
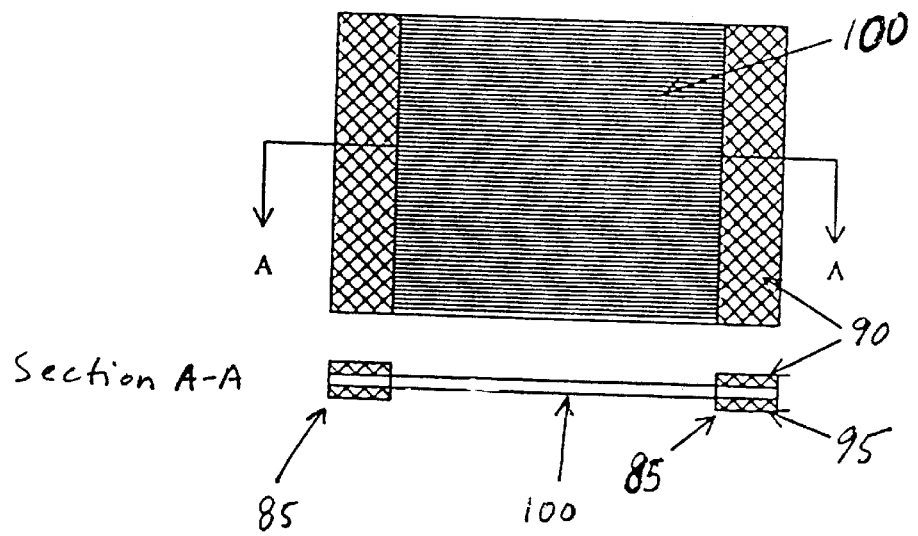
FIG. 18 is a schematic diagram of a degradable sheet having multiple longitudinal slots precut therein and having uncut sections at the edges which incorporate prescribed locking patterns on the surfaces.

Looking at FIG. 18, prescribed sections 85 at both ends of sheet 15 may be thicker than the rest of sheet 15. In a preferred embodiment, sections 85 have a specific male pattern 90 on one side and matching female pattern 95 on the other. The matching male and female patterns 90, 95 contact and inter-digitate when sheet 15 is rolled up. These interdigitations at both ends of the sheet prevent sliding between adjacent layers of the rolled-up structure to maintain a stable, slender structure 35. Also, the slightly greater thickness at both ends helps to separate the layers to provide room for cellular growth between the layers.

In this configuration, a middle thinner portion 100 of sheet 10 has many tiny strips 105. These strips 105 are made with multiple longitudinal slits pre-cut into the material. The slits start and end at a prescribed distance from the edge of the rectangular material to leave uncut margins 30 connecting the adjacent strips 105. These uncut margins 30 form the earlier mentioned thicker sections preferably having interlocking patterns. Each of the tiny strips 105 has longitudinal microchannels 201. These microchannels each have a width and depth of the order of 1 to 200 microns. The sheet may be hydrophilised and coated with collagen and growth factors such as TGF beta, IGF, etc.

Cell seeding may be performed using various methods consistent with the present invention. Several such methods will now be set forth by way of example but not limitation.

Example I

One method involves clamping sheet 15 at both ends 80 of the thicker, uncut sections and immersing the sheet in a culture medium 110. Sheet 15 is initially held in tension and mesenchymal stem cells or fibroblasts are introduced into culture medium 110 and onto strips 105. Cells 25 are allowed to attach to strips 105 and proliferate. Nutrients and growth factors are added periodically as desired. To increase the rate at which the number of cells 25 increase, the mesenchymal stem cells or fibroblast can be genetically altered to increase local production of desired growth factors. This can be done by viral transfection or by incorporating plasmid genes into the matrix of the biocompatible material.

Figure 19:
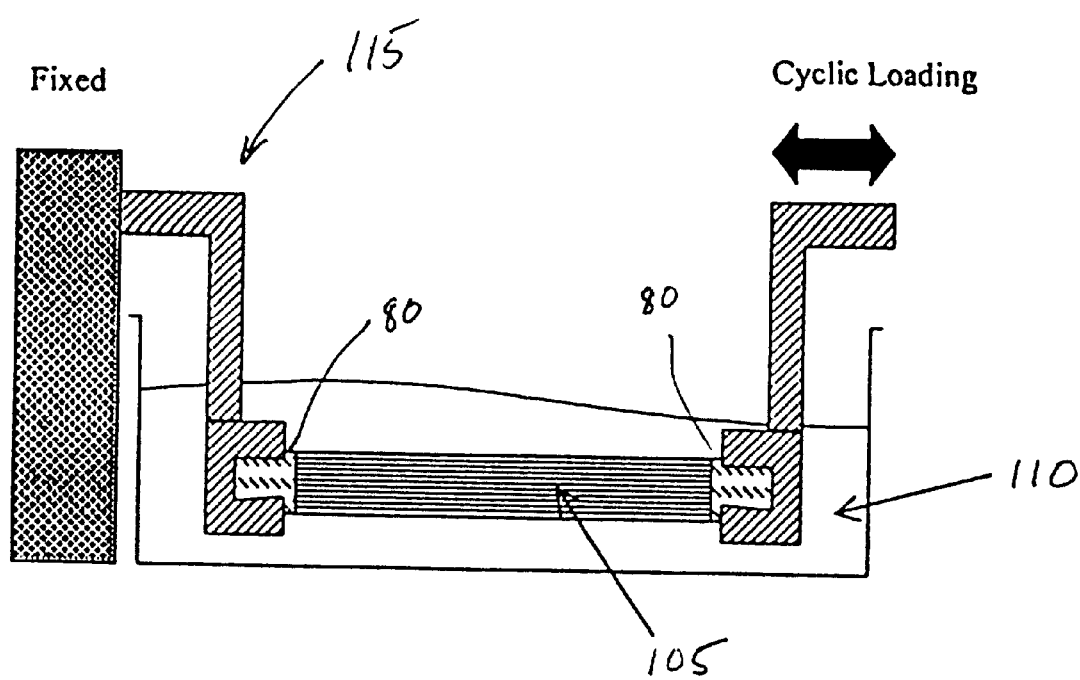
FIG. 19 is a schematic diagram of a rolled-up slender structure immersed in culture medium with mesenchymal stem cells seeded therein, undergoing cyclic tensile loading.

The mesenchymal stem cells are directed to differentiate into fibroblasts and subsequently to fibrocytes. Differentiation occurs under suitable conditions such as exposure to growth factors. Matrix materials are then produced by the fibrocytes. A cyclic tensile load introduced through sheet 15 stimulates the fibrocytes to orientate and align in the direction of tension. Fibrous tissue forms on sheet 15 over a period of time and sheet 15 is then rolled up along strips 105. The ends 80 of sheet 15 are crimped and then clamped in a cyclic loading machine as schematically depicted in FIG. 19. Further cyclic tensile load is applied to the structure immersed in culture medium 110 to promote growth, organization and maturation of cells 25. Tissue-engineered ligament 10 is then implanted into a patient when there is sufficient maturation.

Example II

Another method for cell seeding involves clamping sheet 15 at both ends 80 of the patterned sections 90, 95 and immersing sheet 15 in culture medium solution 110. Sheet 15 is initially held in tension and mesenchymal stem cells or fibroblasts are introduced into solution 110 and onto strips 105. Cells 25 are allowed to attach to strips 105 and proliferate. Nutrients and growth factors are added periodically. To increase the rate at which the number of cells 25 increase, the mesenchymal stem cells or fibroblast can be genetically altered to increase local production of desired growth factors. This can be done by viral transfection or by incorporating plasmid genes into the matrix of the biocompatible material.

Once there is evidence of cell adhesion, sheet 15 is rolled-up along the strips 105 to form a slender structure 35. Ends 80 are then crimped and then clamped. As the rolled-up slender structure 35 continues to be immersed in culture medium 110, a cyclic tensile load is applied to structure 35. The mesenchymal stem cells now differentiate into fibroblasts and secretion of matrix materials takes place. The fibroblasts form fibrocytes and these fibrocytes become aligned in the direction of tension. Over a period of time, the fibrocytes mature into fibrous tissue which forms over rolled-up slender structure 35.

Example III

A third method involves forming a slender structure 35 by any of the methods previously described. Both ends 80 are crimped and clamped, and immersed in culture medium solution 110. The slender structure 35 is initially held in slight tension and mesenchymal stem cells are introduced into the solution and onto the slender structure 35. The cells attach to strips 105 and proliferate. Nutrients and growth factors are added periodically as desired. To increase the rate at which the number of cells 25 increase, the mesenchymal stem cells or fibroblast can be genetically altered to increase local production of desired growth factors. This can be done by viral transfection or by incorporating plasmid genes into the matrix of the biocompatible material.

The mesenchymal stem cells are directed to differentiate into fibroblasts and subsequently to fibrocytes under suitable conditions, including exposure to growth factors. Matrix materials are then produced by the fibrocytes. A cyclic tensile load is introduced to slender structure 35. As the ends of the slender structure 35 move towards and away from one another, the space between strips 105 opens and closes, thereby permitting cells and nutrients to flow between the strips, and thereby giving the cells the opportunity to attach to the interior of the structure. This loading also stimulates cells 25 further. The fibrocytes orientate and align in the direction of tension. Over a period of time, the fibrocytes mature into fibrous tissue which forms over slender structure 35.

The in-vitro tissue-engineered ligament is ready for implantation once ligamentous tissue has formed on slender structure 35. Crimped ends 80 of in-vitro tissue-engineered ligament 10 are then inserted and secured into bone tunnels 65. Preferably, tissue-engineered ligament 10 is secured with interference screws 70. Alternatively, other methods well known in the art may be used.

Initially, the material of scaffold sheet 15 of tissue-engineered ligament 10 supports loading across the joint. For scaffold sheet 15 made of biodegradable material, as the scaffold material of the implanted tissue-engineered ligament 10 degrades over time, the load is gradually transferred to the newly formed tissue. Eventually, when scaffold sheet 15 is completely absorbed, the entire load is transferred to the newly formed tissue of ligament 10.

The preferred embodiments described above contain many examples which are not limitations on the scope of the invention but illustrations of alternate embodiments. Many other variations are possible within the scope of the invention, as those skilled in the art will recognize from the following claims.

What is claimed is:

1. An apparatus for reconstruction of a previously torn ligament, said apparatus comprising:
   a scaffold of biocompatible material, the scaffold having at least one layer forming a scaffold sheet, and the scaffold sheet containing at least one slit;
   means for seeding the scaffold sheet with fibrocyte forming cells to form a seeded scaffold;
   means for increasing the number of the fibrocyte forming cells seeded on the scaffold to create a tissue-engineered scaffold; and
   means for forming a slender structure from the tissue-engineered scaffold, the slender structure being a tissue-engineered ligament suitable for implantation into a patient for reconstruction of a ligament.

2. The apparatus of claim 1 wherein the scaffold sheet is bioabsorbable.

3. The apparatus of claim 1 wherein the scaffold sheet is porous.

4. The apparatus of claim 3 wherein the porous scaffold sheet forms at least one perforation.

5. The apparatus of claim 1 wherein the seeding means is a cultured medium containing the fibrocyte forming cells, the scaffold sheet being placed into the cultured medium for seeding with fibrocyte forming cells.

6. The apparatus of claim 1 wherein the fibrocyte forming cells increasing means is incubation of the scaffold sheet.

7. The apparatus of claim 1 wherein the slender structure forming means is a rolled tubular structure formed by rolling the scaffold sheet.

8. The apparatus of claim 1 wherein the slender structure forming means is an accordion structure formed by folding the scaffold sheet.

9. The apparatus of claim 1 wherein the slender structure forming means is a series of strips cut from the scaffold sheet and the series of scaffold strips are stacked on top of one another.

10. The apparatus of claim 1 wherein threads are molded into each end of the tissue-engineered ligament.

11. The apparatus of claim 1 wherein the scaffold sheet has an interlocking surface along a first section and a second section whereby portions of the first section and the second section interlock with corresponding portions of the first section and the second section when the slender structure is formed from the scaffold sheet.

12. The apparatus of claim 11 wherein the first interlocking section and the second interlocking section each contain a male pattern on one side and a female pattern on the opposite side.

13. The apparatus of claim 1 wherein the tissue-engineered ligament has opposed end margins connected by strips, the end margins having a greater thickness than the strips, wherein the configuration of the strips acts as scaffolding for the fibrocyte forming cells to grow therein.

14. The apparatus of claim 1 further comprising means for cyclic tensile loading prior to implantation.

15. The apparatus of claim 1 wherein the fibrocyte forming cells are mesenchymal stem cells.

16. The apparatus of claim 1 wherein the fibrocyte forming cells are fibroblast cells.

17. The apparatus of claim 1 wherein the fibrocyte forming cells increasing means includes implantation in a penultimate location of a patient's body prior to implantation in a functional location.

18. The apparatus of claim 1 wherein the scaffold sheet includes one or more of the group comprising polyglycolic acid, polyactic acid, a mixture of PGA/PLA, chitin, collagen, autograft tissue, and allograft tissue.

19. The apparatus of claim 18 wherein the tissues are fascia lata.

20. The apparatus of claim 1 wherein the scaffold sheet is coated with a material to promote adhesion of the fibrocyte forming cells.

21. The apparatus of claim 20 wherein the coating material is collagen.

22. A method of making a tissue-engineered ligament, said method comprising:
 forming a scaffold sheet of biocompatible material having at least one layer;
 seeding the scaffold sheet with fibrocyte forming cells to form a seeded scaffold of at least one sheet;
 increasing the number of the fibrocyte forming cells on the seeded scaffold to create a tissue-engineered scaffold; and
 forming a slender structure from the tissue-engineered scaffold, the slender structure being a tissue-engineered ligament suitable for implantation into a patient for reconstruction of a ligament.

23. The method of claim 22 further comprising attaching each end of the tissue-engineered ligament to implantation sites within a patient.

24. The method of claim 22 wherein the scaffold is a single sheet.

25. The method of claim 22 wherein the scaffold is slit at least once, the slit is made in the direction of a first end of the scaffold to a second end of the scaffold, and the slit terminates prior to the first end and the second end.

26. The method of claim 22 wherein seeding the scaffold with fibrocyte forming cells includes placing the scaffold into a cultured medium containing the fibrocyte forming cells.

27. The method of claim 22 wherein increasing the number of fibrocyte cells includes incubating the scaffold sheet after seeding.

28. The method of claim 23 wherein increasing the number of fibrocyte cells further includes incubating the tissue-engineered ligament after forming the slender structure.

29. The method of claim 22 wherein increasing the number of fibrocyte cells includes incubating the tissue-engineered ligament after forming the slender structure.

30. The method of claim 22 wherein forming a slender structure includes rolling the scaffold sheet to form a rolled tubular structure.

31. The method of claim 22 wherein forming a slender structure includes folding the scaffold sheet to form an accordion structure.

32. The method of claim 22 wherein forming a slender structure includes cutting a series of strips from the scaffold sheet and stacking the series of strips on top of one another to form the slender structure.

33. The method of claim 23 wherein attaching each end of the ligament to implantation sites within a patient involves using an interference screw for fixation.

34. The method of claim 22 further comprising molding threads into each end of the tissue-engineered ligament for implantation.

35. The method of claim 22 further comprising providing interlocking surfaces on the scaffold sheet for locking the scaffold sheet into the tissue-engineered ligament when the method step of forming a slender structure is accomplished.

36. The method of claim 22, further comprising applying cyclic tensile loading of the seeded scaffold prior to implantation to increase the strength of the scaffold.

37. The method of claim 22 further comprising applying cyclic tensile loading of the slender structure prior to implantation to strengthen the tissue-engineered scaffold.

38. The method of claim 22 further comprising forming spaces within the slender structure to allow the fibrocyte forming cells to grow therein.

39. The method of claim 22 wherein increasing the number of fibrocyte forming cells further comprises implanting the seeded scaffold in a penultimate section of a patient's body prior to implantation in a functional location.

40. The method of claim 22 wherein increasing the number of fibrocyte forming cells further comprises implanting the slender structure in a penultimate location of a patient's body prior to implantation in a functional location.

41. The method of claim 22 further comprising coating the scaffold sheet with a material to promote adhesion of the fibrocyte forming cells.

42. The method of claim 22 further comprising genetically altering fibrocyte forming cells to increase production of fibrocyte cells.

43. The apparatus of claim 1 wherein the apparatus further comprises:

means for attaching each end of the tissue-engineered ligament to implantation sites within a patient.

44. The apparatus of claim 1 wherein the apparatus further comprises:

means for forming microchannels in the scaffold sheet.

45. The method of claim 22 further comprising forming microchannels in the scaffold sheet.

46. An apparatus for reconstruction of a previously torn ligament, said apparatus comprising:

a scaffold of biocompatible material, the scaffold having at least one layer forming a scaffold sheet;

means for seeding the scaffold sheet with fibrocyte forming cells to form a seeded scaffold;

means for increasing the number of the fibrocyte forming cells seeded on the scaffold to create a tissue-engineered scaffold; and means for forming a slender structure from the tissue-engineered scaffold, the slender structure being a tissue-engineered ligament suitable for implantation into a patient for reconstruction of a ligament, and the tissue-engineered ligament having threads molded into each end thereof.

47. An apparatus for reconstruction of a previously torn ligament, said apparatus comprising:

a scaffold of biocompatible material, the scaffold having at least one layer forming a scaffold sheet;

means for seeding the scaffold sheet with fibrocyte forming cells to form a seeded scaffold;

means for increasing the number of the fibrocyte forming cells seeded on the scaffold to create a tissue-engineered scaffold; and means for forming a slender structure from the tissue-engineered scaffold, the slender structure being a tissue-engineered ligament suitable for implantation into a patient for reconstruction of a ligament;

wherein the scaffold sheet has an interlocking surface along a first section and a second section whereby portions of the first section and the second section interlock with corresponding portions of the first section and the second section when the slender structure is formed from the scaffold sheet.

48. An apparatus for reconstruction of a previously torn ligament, said apparatus comprising:

a scaffold of biocompatible material, the scaffold having at least one layer forming a scaffold sheet;

means for seeding the scaffold sheet with fibrocyte forming cells to form a seeded scaffold;

means for increasing the number of the fibrocyte forming cells seeded on the scaffold to create a tissue-engineered scaffold; and means for forming a slender structure from the tissue-engineered scaffold, the slender structure being a tissue-engineered ligament suitable for implantation into a patient for reconstruction of a ligament, and the tissue-engineered ligament having opposed end margins connected by strips, the end margins having a greater thickness than the strips, wherein the configuration of the strips acts as scaffolding for the fibrocyte forming cells to grow therein.

49. An apparatus for reconstruction of a previously torn ligament, said apparatus comprising:

a scaffold of biocompatible material, the scaffold having at least one layer forming a scaffold sheet;

means for seeding the scaffold sheet with fibrocyte forming cells to form a seeded scaffold;

means for increasing the number of the fibrocyte forming cells seeded on the scaffold to create a tissue-engineered scaffold;

means for forming a slender structure from the tissue-engineered scaffold, the slender structure being a tissue-engineered ligament suitable for implantation into a patient for reconstruction of a ligament; and means for cyclic tensile loading prior to implantation.

50. An apparatus for reconstruction of a previously torn ligament, said apparatus comprising:

a scaffold of biocompatible material, the scaffold having at least one layer forming a scaffold sheet;

means for seeding the scaffold sheet with fibrocyte forming cells to form a seeded scaffold;

means for increasing the number of the fibrocyte forming cells seeded on the scaffold to create a tissue-engineered scaffold; and means for forming a slender structure from the tissue-engineered scaffold, the slender structure being a tissue-engineered ligament suitable for implantation into a patient for reconstruction of a ligament;

wherein the fibrocyte forming cells increasing means includes implantation in a penultimate location of a patient's body prior to implantation in a functional location.

51. An apparatus for reconstruction of a previously torn ligament, said apparatus comprising:

a scaffold of biocompatible material, the scaffold having at least one layer forming a scaffold sheet;

means for seeding the scaffold sheet with fibrocyte forming cells to form a seeded scaffold;

means for increasing the number of the fibrocyte forming cells seeded on the scaffold to create a tissue-engineered scaffold; and means for forming a slender structure from the tissue-engineered scaffold, the slender structure being a tissue-engineered ligament suitable for implantation into a patient for reconstruction of a ligament;

wherein the scaffold sheet comprises fascia lata tissue.

52. An apparatus for reconstruction of a previously torn ligament, said apparatus comprising:

a scaffold of biocompatible material, the scaffold having at least one layer forming a scaffold sheet;

means for seeding the scaffold sheet with fibrocyte forming cells to form a seeded scaffold;

means for increasing the number of the fibrocyte forming cells seeded on the scaffold to create a tissue-engineered scaffold;

means for forming a slender structure from the tissue-engineered scaffold, the slender structure being a tissue-engineered ligament suitable for implantation into a patient for reconstruction of a ligament; and means for forming microchannels in the scaffold sheet.

53. The apparatus of claim 43 wherein the means for attaching is an interference screw for fixation of the end of each ligament at the implantation site.

\* \* \* \* \*